(12) United States Patent
Grobler et al.

(10) Patent No.: US 10,980,646 B2
(45) Date of Patent: Apr. 20, 2021

(54) FEMORAL HEAD MEASUREMENT DEVICE

(71) Applicant: Peninsula Orthopaedics (Pty) Ltd, Cape Town (ZA)

(72) Inventors: Garth Peter Grobler, Cape Town (ZA); Brendan John Dower, Paarl (ZA)

(73) Assignee: PENINSULA ORTHOPAEDICS (PTY) LTD, Cape Town (ZA)

( * ) Notice: Subject to any disclaimer, the term of this patent is extended or adjusted under 35 U.S.C. 154(b) by 128 days.

(21) Appl. No.: 15/565,566

(22) PCT Filed: Nov. 10, 2015

(86) PCT No.: PCT/IB2015/058658
§ 371 (c)(1),
(2) Date: Oct. 10, 2017

(87) PCT Pub. No.: WO2016/166587
PCT Pub. Date: Oct. 20, 2016

(65) Prior Publication Data
US 2018/0116822 A1 May 3, 2018

(30) Foreign Application Priority Data
Apr. 14, 2015 (ZA) .................................. 2015/02483

(51) Int. Cl.
*A61F 2/46* (2006.01)
*A61B 5/00* (2006.01)
(Continued)

(52) U.S. Cl.
CPC .......... *A61F 2/4657* (2013.01); *A61B 5/1072* (2013.01); *A61B 5/4504* (2013.01);
(Continued)

(58) Field of Classification Search
CPC ... A61B 5/1072; A61B 5/4504; A61B 5/4571; A61B 5/4528; A61B 2090/061;
(Continued)

(56) References Cited

U.S. PATENT DOCUMENTS 2,219,596 A * 10/1940 Lundquist .............. B43K 31/00
211/69.8
5,578,037 A * 11/1996 Sanders ................. A61B 17/15
606/102
(Continued)

FOREIGN PATENT DOCUMENTS

CN 101102724 A 1/2008
CN 201701336 U 1/2011
(Continued)

OTHER PUBLICATIONS

Supplementary European Search Report from European International Application No. EP 15 88 9116 dated Mar. 5, 2018, 1 page.
(Continued)

*Primary Examiner* — Marcela I. Shirsat
(74) *Attorney, Agent, or Firm* — Tucker Ellis LLP

(57) ABSTRACT

A measurement device is provided for measuring a resected femoral head. The device comprises a base (102) with a support rod (104) extending transversely from the base and extending in a direction corresponding to a height of a resected femoral head. A femoral head support (108) is attached to a base proximate an end of the support rod (104) for supporting a severed end of a femoral head at a selected incline between about 30° and 60° relative to the base such that a height of the resected femoral head extends in the general direction of the support rod. A transverse height indicating arm (120) is adjustable up the height of the support rod (104) so as to measure the height of a resected femoral head (106) positioned on the femoral head support in use. The transverse height indicating arm (120) may carry adjustable offset indicating arm (122).

12 Claims, 3 Drawing Sheets

(51) Int. Cl.
    *A61B 5/107*     (2006.01)
    *G01B 3/20*     (2006.01)
    *A61B 90/00*     (2016.01)
    *A61F 2/36*     (2006.01)
    *A61B 17/15*     (2006.01)
    *G01B 5/06*     (2006.01)

(52) U.S. Cl.
    CPC .............. *A61B 5/4571* (2013.01); *G01B 3/20* (2013.01); *A61B 5/4528* (2013.01); *A61B 17/155* (2013.01); *A61B 2090/061* (2016.02); *A61B 2505/05* (2013.01); *A61F 2/36* (2013.01); *A61F 2/3609* (2013.01); *A61F 2002/3611* (2013.01); *A61F 2002/4658* (2013.01); *G01B 5/061* (2013.01)

(58) Field of Classification Search
    CPC ... A61B 17/157; A61B 17/154; A61B 17/155; A61F 2/4657; A61F 2/3609; A61F 2002/3611; A61F 2002/4658; A61F 2/36; G01B 3/20; G01B 3/04; G01B 3/38; G01B 5/02; G01B 5/06; G01B 5/061
    USPC ............ 606/102; 33/511–512, 1 V, 3 B, 427, 33/464, 712, 806, 833, 313
    See application file for complete search history.

(56) References Cited

U.S. PATENT DOCUMENTS

| | | | |
|---|---|---|---|
| 5,607,431 A * | 3/1997 | Dudasik | A61B 17/15 606/102 |
| 5,792,143 A | 8/1998 | Samuelson | |
| 5,968,051 A * | 10/1999 | Luckman | A61B 17/8802 606/86 R |
| 6,120,510 A * | 9/2000 | Albrektsson | A61B 17/15 606/96 |
| 7,488,324 B1 * | 2/2009 | Metzger | A61B 17/155 33/511 |
| 8,834,486 B2 | 9/2014 | Metzger | |
| 2005/0273115 A1 * | 12/2005 | Coon | A61B 17/157 606/88 |
| 2008/0208203 A1 | 8/2008 | Moindreau | |
| 2011/0295144 A1 | 12/2011 | Murakawa et al. | |
| 2012/0143205 A1 * | 6/2012 | Dower | A61B 5/1072 606/102 |

FOREIGN PATENT DOCUMENTS

| | | |
|---|---|---|
| CN | 201831894 U | 5/2011 |
| CN | 104394805 A | 3/2015 |
| DE | 3737993 A1 | 11/1989 |
| EP | 1605838 B1 | 6/2009 |
| EP | 2440132 B1 | 12/2010 |
| WO | 2004010382 A1 | 1/2004 |
| WO | 2004084740 A1 | 10/2004 |
| WO | 2010142980 A1 | 12/2010 |
| WO | 2014006360 A1 | 1/2014 |

OTHER PUBLICATIONS

Austrian Patent Office, International Search Report and Written Opinion for corresponding application PCT/IB2015/058658, dated Jan. 26, 2016, pp. 1-8.

* cited by examiner

FEMORAL HEAD MEASUREMENT DEVICE

RELATED APPLICATION DATA

This application is a national phase application of International Application No. PCT/IB2015/058658 filed Nov. 10, 2015 and published in the English language, which claims priority to South African Application No. 2015/02483 filed Apr. 14, 2015, which are hereby incorporated herein by reference.

CROSS-REFERENCE(S) TO RELATED APPLICATIONS

This application claims priority from South African provisional patent application number 2015/02483 filed on 14 Apr. 2015, which is incorporated by reference herein.

FIELD OF THE INVENTION

This invention relates to a femoral head measurement device that is aimed primarily at enabling a target post-operative length of femur and attached hip prosthesis to be achieved which in turn dictates leg length. In particular, it relates to a measurement device for measuring the size of a resected head of a femur in order to select a suitably sized prosthesis and to ensure the correct position during hip replacement surgery or the like.

BACKGROUND TO THE INVENTION

Total or partial hip replacement is a surgical operation generally aimed at replacing a damaged or diseased hip joint or femoral head with a prosthetic hip joint or femoral head.

The difference between the dimensions of the resected bone and the implanted prosthesis dictates any final change in leg length. The resected bone is difficult to measure as it is a complex 3 dimensional shape and the inferior reference point needs to be adjustable to accommodate different prosthesis designs. In order to locate the inferior point of reference consideration needs to take into account the position of the most medial point of the component at the base of the femoral neck in relation to a point on the inner calcar. An example of a reference point is indicated by the letter "A" in FIG. 3.

A total hip replacement replaces the acetabulum (socket) and the head of a femur with a prosthetic or artificial joint. The prosthetic joint comprises a femoral stem that is configured to extend into the hollow canal of the femur, a femoral head component and an acetabular cup component. The femoral head component consists of a round ball that mimics the shape of a femur head and a neck portion. The round ball is configured to fit, at least partially, inside the acetabular cup component. The prosthesis may be manufactured from a variety of different materials having suitable properties.

In a natural hip joint or a prosthetic hip joint assembled in vivo, the neck portion of the femoral head component is at an angle that ranges between about 135° and about 145° relative to the longitudinal axis of the femur. During an exemplary total or partial hip replacement a cross sectional cut is made in an upper region of the femur proximate or through the neck that carries the femoral head. The cut is made at an angle that is approximately at right angles to the angle at which the neck is inclined relative to the femur. This angle should correspond with the neck shaft angle of the planned prosthesis. The resected femoral head and neck is removed from the hip joint, at which time it is necessary to replace it with a prosthetic femoral head component of the correct size and configuration.

In particular, the vertical distance that a femoral head component spans in use is an important dimension of the prosthesis as it will dictate the leg length of a patient. In the context of the in vivo position of a natural femoral head in a standing person, the vertical distance may also be referred to as the "vertical drop" to the neck resection level. This "vertical drop" corresponds to the height of a resected femoral head.

It is necessary to obtain an accurate measurement of the height of a resected femoral head in order to select and prepare the prosthetic femoral head component for proper positioning of the femoral head. The appropriately sized prosthesis can be selected in order to obtain a desired leg length that may be the same or different from the original leg length. In addition, an accurate measurement of a lateral offset of the resected femoral head is needed. The lateral offset corresponds to a crosswise length of the femoral head in its in vivo position. The lateral offset of the prosthesis should be optimised to ensure correct muscle tension in the muscles surrounding the hip joint.

A multitude of implants are available with varying dimensions and therefore an App has been developed utilising the following formula to calculate the leg length during surgery.

Formula: Measured resection−centre of rotation elevation=Cup radius+Implant leg adjustment distance+implant height above reference point.

Digital X-ray images are commonly used as templates for pre-operative planning, i.e. to estimate where the cross-sectional cut through the femur is aimed to be made, to estimate corrections that must be realised in the prosthesis to obtain a target leg length, and so forth. Predicting the vertical height and lateral offset to be effected by the prosthesis intra-operatively may be challenging. A number of techniques have been described to assess leg length correction intra-operatively. None of these methods have been shown to be accurate.

It should be mentioned that leg length is of great importance in the conduct of hip replacement surgery because if the post-operative leg length is not within acceptable limits the surgeon responsible may be exposed to serious malpractice litigation.

There is thus a need to alleviate such difficulties, at least to some extent.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a measurement device for measuring a resected femoral head comprising a base with a support rod extending transversely from the base and extending in a direction corresponding to a height of a resected femoral head;

a femoral head support attached to the base proximate an end of the support rod wherein the femoral head support is configured to support a severed end of a femoral head at a selected incline relative to the base such that a height of the resected femoral head extends in the general direction of the support rod; and, a height indicating arm adjustably secured to the support rod so as to extend transversely from the support rod and configured to be moveable along the height of the support rod so as to measure the height of the resected femoral head positioned on the femoral head support in use.

Further features of the invention provide for the femoral head support to define a support surface that is inclined relative to the base at an angle of between about 35° and 60° to the base; for the angle of inclination of the support surface to be either adjustable, preferably in a stepwise manner or to be defined by a selected one of a plurality of different inserts each of which defines an angle of inclination with the base; for the support surface to be provided with a receiving formation configured to receive and locate a femoral head in position on the inclined support surface; and for the receiving formation to be an upstanding pin.

A further feature of the invention provides for the measurement device to have an offset indicating arm carried by the height indicating arm and adjustable in position along the length of the height indicating arm so as to measure a lateral offset of a resected femoral head in use.

Yet a further feature of the invention provides for the base to include a recess or slot configured to accommodate a portion of a femoral head that extends in the general direction of the base in use. This allows positioning of the resected femoral head to ensure that the measurement corresponds to the pre-determined reference point of the planned prosthesis.

Still further features of the invention provide for the support rod and the height indicating arm to include graduations that denote distances or indicators that corresponds with different sizes and configurations of prosthetic femoral heads and femoral stems.

BRIEF DESCRIPTION OF THE DRAWINGS

The invention will now be described, by way of example only, with reference to the accompanying drawings in which.

DETAILED DESCRIPTION WITH REFERENCE TO THE DRAWINGS

Figure 1:
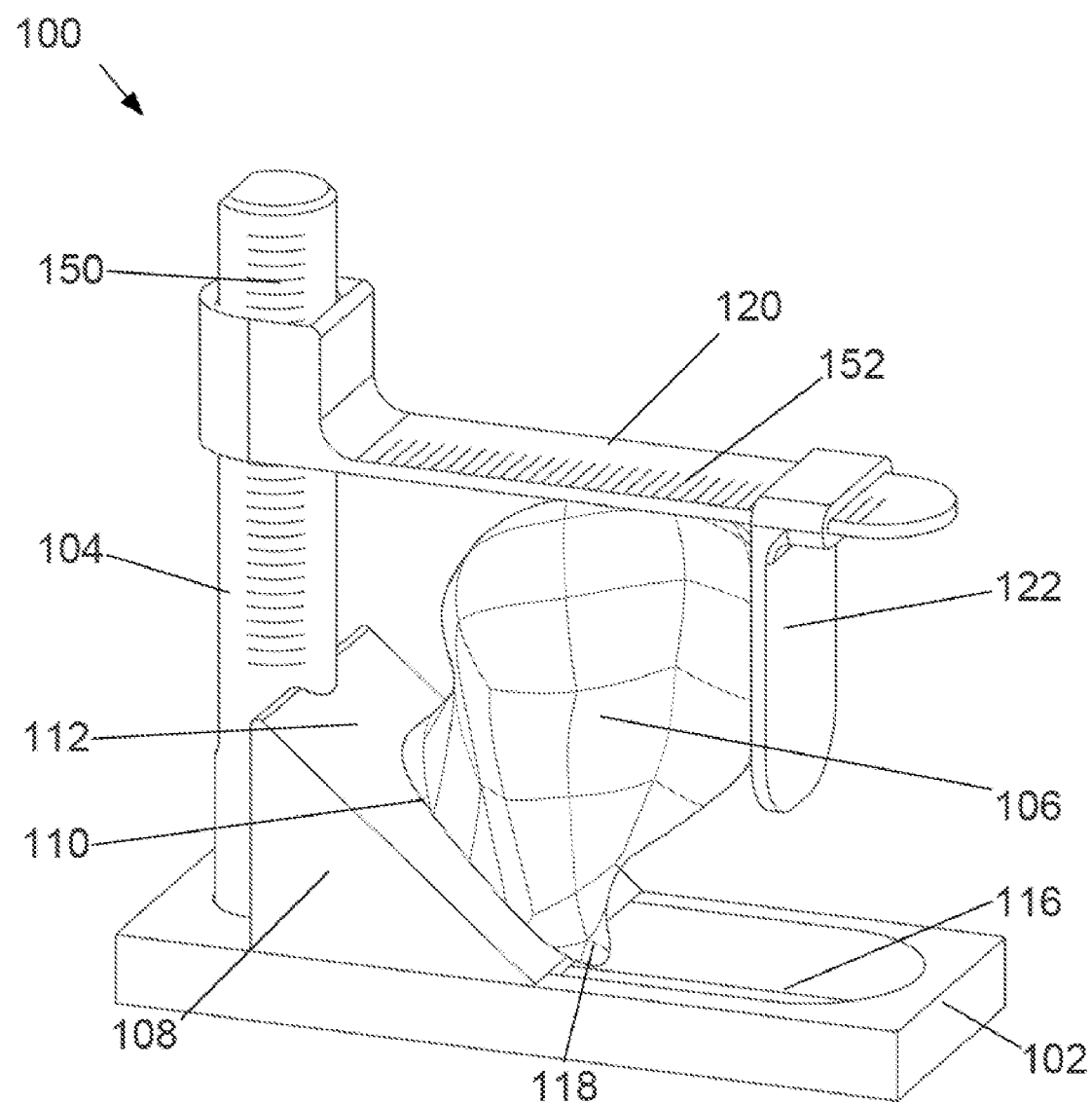
FIG. 1 is a schematic three dimensional illustration of an embodiment of the measurement device in accordance with the invention when it is in use measuring a resected femoral head.
Figure 2:
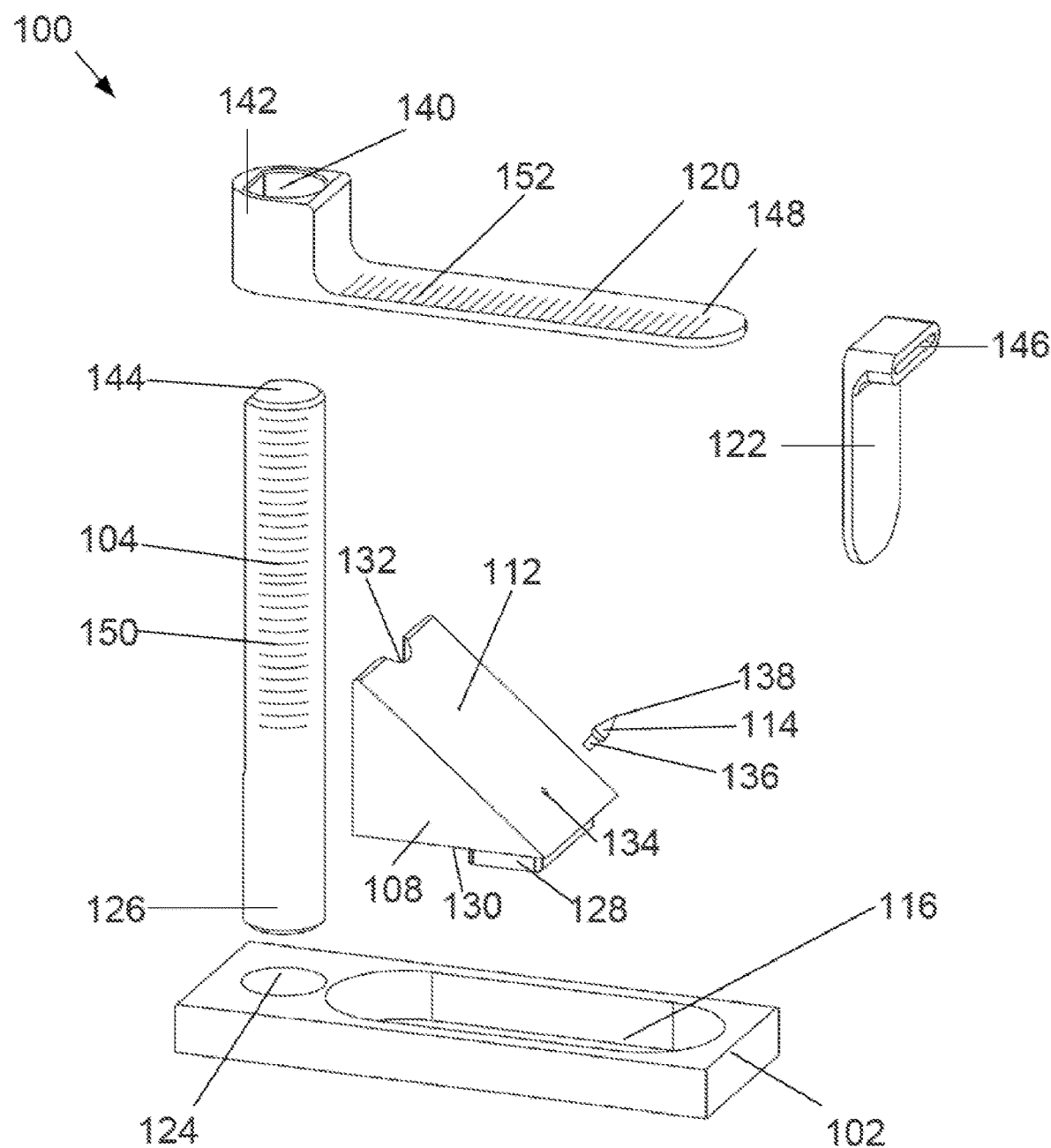
FIG. 2 is a schematic exploded three dimensional illustration of the embodiment of measurement device illustrated in FIG. 1.
Figure 3:
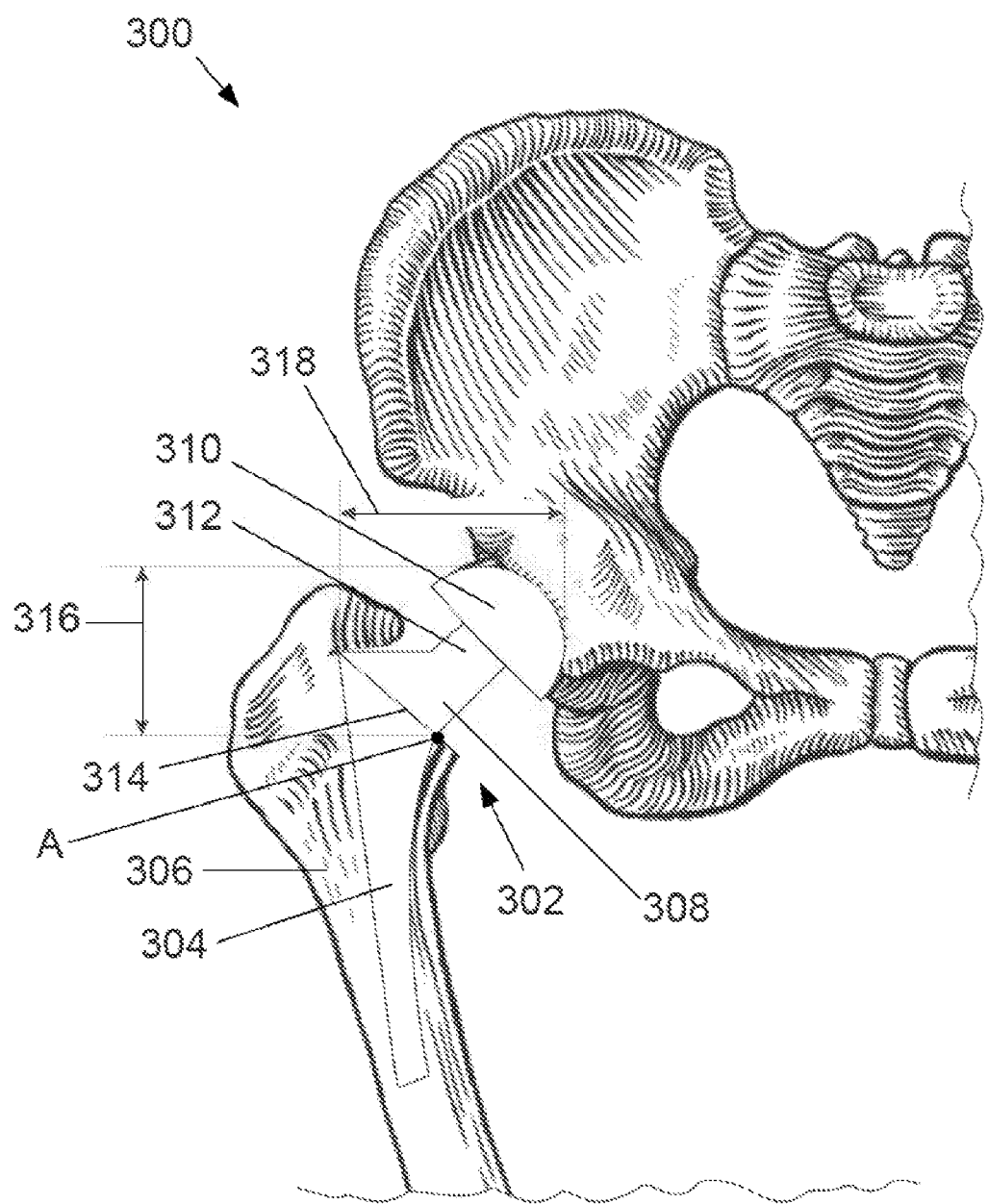
FIG. 3 is an illustration of a part of a human skeleton which includes a prosthetic hip joint viewed from the front.

An embodiment of a measurement device (100) for measuring a resected femoral head in accordance with the invention is shown in FIGS. 1 and 2. The measurement device (100) includes a base (102) and a support rod (104) extending transversely from the base (102). The support rod (104) extends in a direction corresponding to a height of a resected femoral head (106) (as indicated in FIG. 3). A femoral head support (108) is located proximate an end of the support rod (104) attached to the base (102). The femoral head support (108) is configured to support a severed end of a femoral head (110) at a selected incline relative to the base (102) such that a height of the severed end of the femoral head (106) extends in the general direction of the support rod (104). In the embodiment shown in FIGS. 1 and 2 the femoral head support is a substantially triangular insert that defines a support surface (112) that is inclined relative to the base (102) at an angle of 45° to the base (102). The support surface (112) is provided with a receiving formation, in this embodiment an upstanding pin (114) that is configured to receive and locate a femoral head (106) in position on the inclined support surface (112).

The base (102) is configured to receive a plurality of different inserts each of which defines an angle of inclination with the base (102) that varies between about 30° and 60° to the base (102). A typical angle is often about 40°. The base (102) includes a slot (116) which is configured to accommodate a lowermost central portion (118) of a resected femoral head that extends in the general direction of the base (102) in use.

A height indicating arm (120) is adjustably attached to the support rod (104) so as to extend transversely from the support rod (104). The height indicating arm (120) is configured to be moveable along the height of the support rod (104) so as to measure the height of the resected femoral head (106) positioned on the femoral head support (108) in use. The support rod (104) may include graduations (150) that denote distances, such as femoral head heights, or indicators that correspond with different sizes and configurations of prosthetic femoral heads and femoral stems.

The height indicating arm (120) carries an offset indicating arm (122). The offset indicating arm (122) is adjustable in position along the length of the height indicating arm (120) so as to measure the lateral offset of a resected femoral head (106) in use. The height indicating arm may include graduations (152) that denote distances, such as offset distances, or indicators that correspond with different sizes and configurations of prosthetic femoral heads and femoral stems.

The embodiment of the measurement device for measuring a resected femoral head shown in FIGS. 1 and 2 has a modular configuration. The measurement device consists of adjoining parts that may be assembled prior to use. The adjoining parts are most clearly shown in FIG. 2 in which the measurement device is illustrated in an exploded condition. The base (102) includes a round slot (124) configured to receive an end (126) of the support rod (104). The femoral head support (108) is an insert that is rectangular in plan view and triangular in side elevation so as to form the inclined support surface, wherein the side that cooperates with the base includes a downwardly projecting locating formation (128). The locating formation (128) is configured to protrude into the slot (116) to locate the femoral head support on the base (102). A curved recess (132) is provided in the femoral head support (108) to accommodate part of the cylindrical support rod (104) when the measurement device (100) is in an assembled condition. The femoral head support (108) defines a hole (134) into which a stem (136) of the upstanding pin (114) is inserted during assembly. The upstanding pin (114) has a sharp free end (138) configured to, if need be, pierce into a resected femoral head.

The height indicating arm (120) defines a channel (140) through a first end (142) thereof that is configured to allow a free end (144) of the support rod (104) to pass through it so as to slideably interact with the support rod (104) to enable the adjustment of the height of the height indicating arm. Similarly, the offset indicating arm has an opening (146) through which a free end (148) of the height indicating arm (120) may pass in use. The offset indicating arm (122) slideably interacts with the height indicating arm (120) by means of the opening (146) such that the offset indicating arm (122) is slideable along the length of the height indicating arm (120).

In use, a severed end (110) of a resected femoral head (106) is mounted on the upstanding pin (114) centrally located on the inclined support surface (112) of the femoral head support (108). The height indicating arm (120) may first have to be manually lifted against the force of gravity or against any frictional supporting force, by sliding it up the height of the support rod (104) and, if necessary, manually held at a position near the free end (144) of the support rod (104) to enable placement of the resected femoral head on the femoral head support (108). A surgical hammer may then be used to locate the femoral head onto the sharp end (138) of the upstanding pin (114). The height indicating arm (120) initially positioned near the upper free end (144) of the support rod (104) is lowered towards the resected femoral head (106) until it abuts against the operatively upper surface of the femoral head (106). Once the rigid height indicating arm (120) rests on the resected femoral head (106), a reading may be taken from the graduations on the support arm. The graduations may indicate distances relating to femoral head height or different sizes and configurations of femoral prostheses.

Next, the offset indicating arm (122), initially located near a free end (148) of the height indicating arm (120) is manually adjusted along the length of the height indicating arm (120) in the direction of the resected femoral head (106) mounted on the femoral head support (108) until the offset indicating arm (122) abuts against a lateral side of the resected femoral head (106). Once the offset indicating arm (122) abuts the resected femoral head (106), a reading may be taken from the graduations on the height indicating arm (120). The graduations may indicate distances relating to the lateral offset of a femoral head or different sizes and configurations of femoral prostheses.

FIG. 3 is an illustration of part of a human skeleton (300) viewed from the front which includes a prosthetic hip joint (302). The prosthetic joint comprises a femoral stem (304) that extends into a hollow canal of the femur (306) in use and a femoral head component (308). The femoral head component (308) consists of a head (310) that may mimic the shape of a femur head and a neck portion (312) that supports the head. In use, the head (310) is received within an acetabular cup (not shown) of a hip joint. During hip replacement surgery a cross-sectional cut, at a planned resection level (314), is made through the femur (306). The cut is at an incline relative to the longitudinal axis of the femur (306). The distance markers in FIG. 3 indicate the important dimensions of the prosthetic femoral head component (308), namely the height (316) and the lateral offset (318) of the femoral head component in its in vivo position. The height (316) measured from the inferior reference point dictates the leg length in a patient and the lateral offset (318) will affect muscle tension and the overall mobility of the hip joint and legs of a patient.

The prosthetic joint comprises a femoral stem that is configured to extend into the hollow canal of the femur, a femoral head component and an acetabular cup component. The femoral head component consists of a round ball that mimics the shape of a femur head and a neck portion. The round ball is configured to fit, at least partially, inside the acetabular cup component.

Many other embodiments of a measurement device for measuring a resected femoral head that fall within the scope of the invention exist. For example, in one embodiment of the measurement device, the height indicating arm of the measurement device includes a releasable engagement formation for releasably engaging the support rod. The releasable engagement formation may be used to secure the height indicating arm at a fixed position along the height of the support rod. Similarly, the offset indicating arm may also be provided with a releasable engagement formation that allows a user to fix the position of the offset indicating arm along the length of the height indicating arm. In this manner, the positions of the height and offset indicating arms can be fixed following a measurement of a resected femoral head. Fixing the arms in position allows for direct comparison of the height and lateral offset measurements of a resected femoral head with the height and lateral offset of a femoral prosthesis. The femoral prosthesis may be placed on or held near the femoral head support of the measurement device for a direct visual comparison.

The above description is by way of example only and it should be appreciated that numerous changes and modifications may be made to the measurement device without departing from the scope of the invention. For example, the measurement device need have a modular configuration, but it could comprise parts that are permanently joined or fixed together with suitable fasteners or adhesives. The modular configuration, does however, allow for easy disassembly, cleaning and sterilization as well as compact storage and transport of the measurement device.

The measurement device may include any suitable receiving formation for receiving and locating the resected femoral head on the femoral head support, such as a clamp or the like. It will be appreciated by those skilled in the art that the manner in which the height and offset indicating arms are adjustably secured to the support rod and height indicating arm to enable movement along the lengths thereof may be altered without departing from the scope of the invention. For example, the support rod may define a slot configured to receive a projection on an end of the height indicating arm, wherein the projection is slideably moveable within the slot. The height and offset indicating arms of the measurement device may be of any suitable shape and size.

The measurement device in accordance with the invention is not only configured to measure the height and lateral offset of a resected femoral head, but it may also be used to measure the height and lateral offset of prosthetic femoral head components.

The measurement device in accordance with the invention may be used in a surgical method or technique involving a total or partial hip replacement. An exemplary surgical method includes the following steps: planning the operation by estimating a resection level in the femur; severing the femoral head according to the planned resection level; measuring the resected femoral head using the measurement device as herein described; comparing the measurements of the resected femoral head to that of one or more prostheses; selecting a prosthesis of a suitable size and configuration to replace the resected femoral head; and inserting the selected prosthesis in the correct position. The step of measuring the resected femoral head using the measurement device includes measuring a height of the resected femoral head as well as a lateral offset of the resected femoral head.

The step of planning the operation involves a pre-operative templating method during which accurate x-ray images with size markers for scale are used to make measurements of a patient's hip joint. An exemplary templating method involves determining the size and position of the implant to ensure correct leg length.

The actual resection level at which the femur is severed may not correspond with the planned or estimated resection level for various reasons. The measurement device according to the invention may then be used to measure the height and lateral offset of a resected femoral head. The measurements of the height and lateral offset of the resected femoral head may be used to select the appropriately sized prosthesis and/or to change or adjust the configuration of a modular prosthesis. For example, in a modular prosthesis the neck height of a femoral head component or the like can be altered to change prosthesis height and offset prior to implantation of the prosthesis in order to obtain a target leg length and offset in a patient. Also, interchangeable femoral head supports may be provided with different angles of inclination of the support surface.

The invention therefore allows the resected femoral head to be measured in 2 planes from specific reference points.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A measurement device for measuring a resected femoral head comprising:
    a base having top and bottom surfaces;
    a support rod extending perpendicular from the top surface of the base and extending in a first direction corresponding to a height of a resected femoral head, the support rod including a plurality of graduations spaced along its height;
    a femoral head support attached to the base and having an inclined support surface inclined at an angle of between 35° and 60° relative to the top surface of the base and extending away from the support rod in a second direction and inclined in a third direction with the inclined support surface inclined along the second direction and configured to support a severed end of the resected femoral head at a selected incline relative to the base such that a height of the resected femoral head extends in the general direction of the support rod; and
    a height indicating arm having a planar measuring surface adjustably secured to the support rod so as to extend transversely from the support rod in the second direction and configured to be moveable along the height of the support rod in the first direction so as to measure the height of the resected femoral head positioned on the femoral head support in use via the graduations on the support rod to which a position of the planar measuring surface is calibrated.

2. A measurement device as claimed in claim 1 in which the angle of inclination of the support surface is either adjustable in a stepwise manner or as defined by a selected one of a plurality of different inserts each of which defines an angle of inclination of the support surface with the base.

3. A measurement device as claimed in claim 1 in which the support surface is provided with a receiving formation configured to receive and locate a femoral head in position on the inclined support surface.

4. A measurement device as claimed in claim 3 in which the receiving formation is an upstanding pin.

5. A measurement device as claimed in claim 1 in which the measurement device has an offset indicating arm carried by the height indicating arm and adjustable in position along the length of the height indicating arm so as to measure a lateral offset of a resected femoral head in use.

6. A measurement device as claimed in claim 5 in which the height indicating arm has graduations indicating a measure of a lateral offset of a resected femoral head that denote offset distances or indicators that corresponds with different sizes and configurations of prosthetic femoral heads and femoral stems.

7. A measurement device as claimed in claim 1 in which the height indicating arm includes graduations that denote distances or indicators that corresponds with different sizes and configurations of prosthetic femoral heads and femoral stems.

8. A measurement device as claimed in claim 1 in which the femoral head support is attached to the top surface of the base proximate an end of the support rod.

9. A measurement device as claimed in claim 1 in which the base includes a recess or slot configured to accommodate a portion of a femoral head that extends in the general direction of the base in use.

10. A measurement device as claimed in claim 9 in which the recess or slot enables positioning of the resected femoral head on the femoral head support such that the height is measured from a point on the resected femoral head that corresponds to a pre-determined reference point of a planned prosthesis.

11. A measurement device for measuring a resected femoral head comprising:
    a base having top and bottom surfaces;
    a support rod extending perpendicular from the top surface of the base and extending in a direction corresponding to a height of a resected femoral head;
    a femoral head support attached to the base and having an inclined support surface inclined relative to the top surface of the base and configured to support a severed end of the resected femoral head at a selected incline relative to the base such that a height of the resected femoral head extends in the general direction of the support rod; and
    a height indicating arm adjustably secured to the support rod so as to extend transversely from the support rod and configured to be moveable along a height of the support rod so as to measure the height of the resected femoral head positioned on the femoral head support in use,
    wherein the base includes a recess or slot configured to accommodate a portion of a femoral head that extends in the general direction of the base in use.

12. A measurement device as claimed in claim 11 in which the recess or slot enables positioning of the resected femoral head on the femoral head support such that the height is measured from a point on the resected femoral head that corresponds to a pre-determined reference point of a planned prosthesis.

* * * * *